United States Patent [19]

Storni et al.

[11] Patent Number: 4,772,630
[45] Date of Patent: Sep. 20, 1988

[54] BENZAMIDES AND THEIR SALTS

[75] Inventors: Angelo Storni, Rheinfelden, Switzerland; Serge F. Bischoff, Altkirch-Zaessingue, France; Georg v. Sprecher, Allschwil, Switzerland

[73] Assignee: Ciba-Geigy Corp., Ardsley, N.Y.

[21] Appl. No.: 799,372

[22] Filed: Nov. 18, 1985

[30] Foreign Application Priority Data

Nov. 23, 1984 [CH] Switzerland ............... 5608/84
Jun. 4, 1985 [CH] Switzerland ............... 2363/85

[51] Int. Cl.$^4$ ............... A61K 31/275; C07C 121/75
[52] U.S. Cl. ............... 514/522; 558/415
[58] Field of Search ............... 558/415; 514/522

[56] References Cited

U.S. PATENT DOCUMENTS 3,177,252  4/1965  Leon et al. ............... 544/159
3,219,528  11/1965 Leon et al. ............... 514/331
4,559,349  12/1985 Storni ............... 514/318

FOREIGN PATENT DOCUMENTS 183190   6/1986  European Pat. Off. ............ 514/522
3407654  9/1984  Fed. Rep. of Germany.
A085707  8/1965  France ............... 558/145

OTHER PUBLICATIONS

Abstract of Japan, 50157336, 6/4/74.
Abstract of Netherlands, 7204539, 4/6/71.

Primary Examiner—Anton H. Sutto
Attorney, Agent, or Firm—Irving M. Fishman

[57] ABSTRACT

Benzamides of the formula

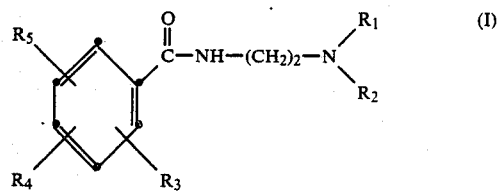

in which $R_1$ and $R_2$, independently of one another, each represents lower alkyl, $R_3$ represents lower alkoxy, $C_3$–$C_5$-alkenyloxy, $C_3$–$C_7$-cycloalkoxy or $C_3$–$C_7$-cycloalkyl-lower alkoxy, $R_4$ represents halogen and $R_5$ represents cyano, and their salts can be used, for example, as pharmaceutical agents and can be manufactured in a manner known per se.

19 Claims, No Drawings

BENZAMIDES AND THEIR SALTS

The invention relates to benzamides of the formula

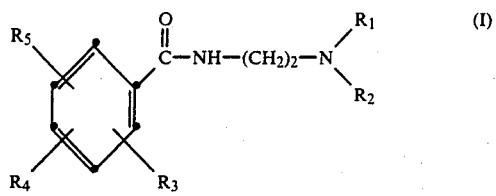

in which $R_1$ and $R_2$, independently of one another, each represents lower alkyl, $R_3$ represents lower alkoxy, $C_3$–$C_5$-alkenyloxy, $C_3$–$C_7$-cycloalkoxy or $C_3$–$C_7$-cycloalkyl-lower alkoxy, $R_4$ represents halogen and $R_5$ represents cyano, and their salts, processes for their manufacture, pharmaceutical preparations containing these compounds or pharmaceutically acceptable salts thereof, and the use of these compounds, for example in a method for the therapeutic treatment of the human or animal body or for the manufacture of pharmaceutical preparations.

Salts of the compounds of the formula I are their acid addition salts, preferably pharmaceutically acceptable acid addition salts. These are formed, for example, with strong inorganic acids, such as mineral acids, for example sulphuric acid, a phosphoric acid or a hydrohalic acid, with strong organic carboxylic acids, such as lower alkanecarboxylic acids, for example acetic acid, such as optionally unsaturated dicarboxylic acids, for example malonic, maleic or fumaric acid, or such as hydroxycarboxylic acids, for example tartaric or citric acid, or with sulphonic acids, such as lower alkane- or optionally substituted benzene-sulphonic acids, for example methane- or p-toluene-sulphonic acid. Also included are salts that are unsuitable for pharmaceutical uses, as these can be used, for example, for isolating or purifying free compounds according to the invention and their pharmaceutically acceptable salts.

Hereinbefore and hereinafter, by radicals or compounds designated "lower" there are to be understood especially those that contain up to and including 7, and especially up to and including 4, carbon atoms.

Lower alkyl is, for example, methyl, ethyl, n-propyl, isopropyl, n-butyl, isobutyl, sec.-butyl or tert.-butyl and also includes corresponding pentyl, hexyl and heptyl radicals.

Lower alkoxy is, for example, methoxy, ethoxy, n-propoxy, isopropoxy, n-butoxy, isobutoxy, sec.-butoxy or tert.-butoxy.

$C_3$–$C_5$-alkenyloxy is, for example, allyloxy, methallyloxy, crotonyloxy or 3,3-dimethylallyloxy.

$C_3$–$C_7$-cycloalkoxy is, for example, cyclopropoxy, cyclobutoxy, cyclopentyloxy or cycloheptyloxy.

$C_3$–$C_7$-cycloalkyl-lower alkoxy is, for example, cyclopropyl-, cyclobutyl-, cyclopentyl- or cyclohexyl-methoxy or -ethoxy.

Halogen is, for example, halogen having an atomic number of up to and including 35, such as fluorine, chlorine or bromine and also iodine.

U.S. Pat. Nos. 3,177,252 and 3,219,528 describe antiemetically active compounds of analogous structure.

Compared therewith, the compounds of the formula I and their pharmaceutically acceptable salts have a novel profile of pharmacological activity.

In the test model described by S. Bischoff et al., European J. Pharmacology 68, 305–315 (1980), on administration of the compounds according to the invention at a dosage of from approximately 1.0 mg/kg upwards in the case of rats, an increase in the in vivo-[$^3$H] spiperone binding in all relevant cerebral structures, especially in the striatum, was detected. This effect indicates a blocking of the presynaptic dopamine (DA) receptors at low doses, which effects an increase in the DA conversion. The positive change in behaviour caused by this stimulation can also be detected in the social interaction test analogously to S. File et al., Pharmacol. Biochem. Behav. 11, 65–69 (1979). In the case of a cumulative active ingredient concentration the postsynaptic DA receptors are blocked, as could be ascertained, at a dosage of from approximately 90 mg/kg upwards in the case of rats, on the basis of the inhibition of the in vivo-[$^3$H] spiperone binding in the pituitary gland where only postsynaptic DA receptors are localised. In the mentioned social interaction test in the case of rats there was observed, as a consequence of this, a suppression of hyperactivity and an inhibition of amphetamine-induced stereotyping.

Especially advantageous is the fact that no extrapyramidal secondary actions were found when using the compounds according to the invention.

For the first time, therefore, active ingredients have been found that at the same time have, at low doses, first a stimulating effect on the psyche and then, at cumulative active ingredient concentrations, a suppressive effect on the psyche.

The compounds of the formula I and their pharmaceutically acceptable salts can accordingly be used as pharmaceutical agents, for example as dopaminergic stimulating anti-depressants and as therapeutic agents having anti-depressant and neuroleptic components, especially for the treatment of chronic schizophrenia and depressive states. The use of the compounds according to the invention includes the commercial production of their active ingredients as well as their therapeutic use.

The invention also relates, therefore, to the therapeutic treatment of the human or animal body and to the use of the compounds according to the invention, for example as therapeutic agents and for the manufacture of pharmaceutical preparations.

The invention relates especially to compounds of the formula I in which $R_1$ and $R_2$, independently of one another, each represents lower alkyl having up to and including 4 carbon atoms, $R_3$ represents lower alkoxy having up to and including 4 carbon atoms, $C_3$–$C_5$-alkenyloxy, $C_3$–$C_7$-cycloalkoxy or $C_3$–$C_7$-cycloalkyl-lower alkoxy having up to and including 4 carbon atoms in the lower alkoxy moiety, $R_4$ represents halogen having an atomic number of up to and including 35 and $R_5$ represents cyano, and their salts.

The invention relates especially to compounds of the formula I, in which $R_1$ and $R_2$ independently of one another, each represents lower alkyl having up to and including 4 carbon atoms, $R_3$ represents lower alkoxy having up to and including 4 carbon atoms, $R_4$ represents halogen having an atomic number of up to and including 35 and $R_5$ represents cyano, and their salts.

The invention relates especially to compounds of the formula

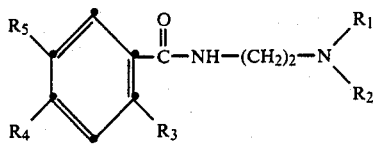 (Ia)

which fall within the scope of the formula I and in which $R_1$, $R_2$, $R_3$, $R_4$ and $R_5$ have the meanings indicated, and their salts.

The invention relates especially to compounds of the formula Ia which fall within the scope of the formula I and in which $R_1$ and $R_2$, independently of one another, each represents lower alkyl having up to and including 4 carbon atoms, $R_3$ represents methoxy or ethoxy, $R_4$ represents chlorine and $R_5$ represents cyano, and their salts.

The invention relates especially to compounds of the formula Ia which fall within the scope of the formula I and in which $R_1$ and $R_2$ represent lower alkyl, especially having up to and including 4 carbon atoms, $R_3$ represents methoxy, $R_4$ represents chlorine and $R_5$ represents cyano, and their salts.

The invention relates especially to compounds of the formula I or Ia in which $R_1$ and $R_2$, independently of one another, each represents lower alkyl in which the sum of the number of carbon atoms is from 4 up to and including 6, and their salts.

The invention relates especially to compounds of the formula I or Ia in which $R_1$ and $R_2$, independently of one another, each represents ethyl or isopropyl, and their salts.

The invention relates especially to the novel compounds mentioned in the Examples.

The present invention also relates to processes for the manufacture of the compounds of the formula I and their salts, characterised in that (a) in a compound of the formula

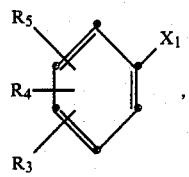 (II)

or in a salt thereof, in which $X_1$ represents a radical that can be converted into the grouping of the formula $-CO-NH-(CH_2)_2-N(R_1)(R_2)$, $X_1$ is converted into the grouping $-CO-NH-(CH_2)_2-N(R_1)(R_2)$, or (b) a compound of the formula

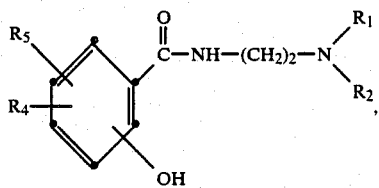 (III)

or a salt thereof, is etherified, or (c) in a compound of the formula

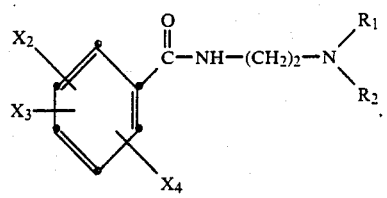 (IV)

or in a salt thereof, in which one of the radicals $X_2$, $X_3$ and $X_4$ represents the diazonium grouping $-N_2^\ominus$ $A^\ominus$ and $A^\ominus$ represents an anion, and the other radicals represent $R_3$, $R_4$ or $R_5$ corresponding to the substitution pattern of the compound of the formula I, the diazonium group is substituted, or (d) in a compound of the formula

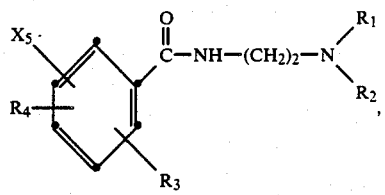 (V)

or in a salt thereof, in which $X_5$ represents a radical that can be converted into cyano, $X_5$ is converted into cyano, and if desired, a salt obtainable according to the process is converted into the free compound of the formula I or into a different salt and/or the free compound obtainable according to the process is converted into a salt.

Starting materials having basic centres can be, for example, in the form of acid addition salts, for example with the acids mentioned above, while starting compound with acids groups, for example carboxy or phenolic hydroxy, can form salts with bases, such as alkali metal, alkaline earth metal, ammonium or amine salts with substituted organic amines.

The reactions described hereinbefore and hereinafter in variants (a) to (d) are carried out according to processes that are known per se, for example in the absence or, customarily, in the presence, of a suitable solvent or diluent or a mixture thereof, the reaction being carried out, depending on the method, while cooling, at room temperature or while heating, for example in a temperature range of from approximately $-20°$ to the boiling temperature of the reaction medium and if necessary, in a closed vessel, under pressure, in an inert gas atmosphere and/or under anhydrous conditions.

The starting materials of the formulae II, III, IV and V mentioned hereinbefore and hereinafter which were developed for the manufacture of the compounds of the formula I and their salts are known in some cases or can be manufactured according to methods that are known per se, for example analogously to the process variants described hereinbefore and hereinafter.

Variant (a)

$X_1$ of the formula II represents, for example, carboxy and functionally modified, especially reactive functionally modified, carboxy. In order to manufacture the compounds of the formula I and their salts, for example carboxy derivatives or reactive functionally modified carboxy derivatives of the formula II are used as starting materials and reacted with the compound of the formula H₂N—(CH₂)₂—N(R₁)(R₂) (IIa) or a salt thereof.

Reactive functionally modified carboxy derivatives of the formula II are, for example, mixed anhydrides and also symmetrical anhydrides, activated esters and activated amides.

As mixed anhydrides there come into consideration, for example, those with inorganic acids, with mixed inorganic acid anhydrides or with inorganic esters, such as carboxylic acid halides, for example the chloride, the carboxylic acid azide, mixed anhydrides with a mixed phosphoric acid anhydride, for example with a phosphoryl halide, or mixed anhydrides with a carbonic acid semiester, for example with a carbonic acid lower alkyl semiester. Mixed anhydrides can also be formed with organic acids, such as with unsubstituted, or, for example, halo-substituted, lower alkanecarboxylic acids, or with organic sulphonic acids, such as with lower alkane- or benzene-sulphonic acids optionally substituted, for example, by halogen or lower alkyl.

By activated esters of the carboxylic acid of formula II there are to be understood, for example, the vinyl ester or activated vinyl ester, such as 1-lower alkoxyvinyl ester or 2-(N-lower alkylcarbamoyl)-1-hydroxysulphonylphenylvinyl ester, aryl(thio)esters, such as phenyl esters that are unsubstituted or substituted, for example by halogen, nitro or phenylhydrazo, or unsubstituted or nitro-substituted phenylthioesters or pyridinium esters, for example 1-lower alkyl-2-pyridinium ester, the cyanomethyl ester, 2-isourea esters, such as 1,3-di-lower alkylisourea ester, 1,3-dicycloalkyl-2-isourea ester or 1-di(phenyl)-lower alkyl-2-isourea ester, or silyl esters, such as tri-lower alkylsilyl esters. There may likewise be mentioned, for example, N-hydroxy esters, such as those that are formed from N-hydroxysuccinimide, N-hydroxyphthalimide, N-hydroxypiperidine or 1,1'-(carbonyldioxy)-dibenzotriazole (leads to the 1-benzotriazole ester).

Activated amides of the formula II are, for example, imidazolides, for example formed from 1,1'-carbonyldiimidazole, or 3,5-disubstituted pyrazolides which may be formed, for example, by reacting the hydrazide with a 1,3-diketone.

The reaction according to the process (N-acylation) is if necessary carried out in the presence of a condensation agent, especially a basic condensation agent. As bases there come into consideration, for example, alkali metal hydroxides, hydrides, amides, alkoxides, carbonates, triphenylmethylides, di-lower alkylamides, aminoalkylamides or lower alkylsilylamides, naphthalinamines, lower alkylamines, basic heterocycles, ammonium hydroxides and carbocyclic amines. By way of example there may be mentioned sodium hydroxide, hydride or amide, potassium tert.-butoxide or carbonate, lithium triphenylmethylide or diisopropylamide, potassium 3-(aminopropyl)-amide or bis-(trimethylsilyl)-amide, dimethylaminonaphthaline, di- or triethylamine, pyridine, benzyltrimethylammonium hydroxide, 1,5-diazabicyclo[4.3.0]non-5-ene (DBN) and 1,8-diazabicyclo-[5.4.0]-undec-7-ene (DBU). The condensation agents also include the dehydrating agents customary in the formation of amide bonds, which are used especially when X₁ of the formula II represents carboxy. It is possible, for example, for reactive carboxy derivatives of the formula II, especially corresponding activated esters or amides, especially of the type indicated above, to be formed in situ. Suitable dehydrating agents are, for example, carbodiimides, for example N,N'-di-lower alkyl- or N,N'-dicycloalkyl-carbodiimides, such as N,N'-diethyl-, N,N'-diisopropyl- or N,N'-dicyclohexyl-carbodiimides, advantageously with the addition of N-hydroxysuccinimide or optionally substituted, for example, halo-, lower alkyl- or lower alkoxy-substituted, 1-hydroxy-benzotriazole or N-hydroxy-5-norbornene-2,3-dicarboxamide, N,N'-diimidazolecarbonyl, a suitable phosphonyl or phosphine compound; for example diethylphosphonyl cyanide, diphenylphosphonyl azide or triphenylphosphine disulphide, a 1-lower alkyl-2-halopyridinium halide, for example 1-methyl-2-chloropyridinium iodide, a suitable 1,2-dihydroquinoline, for example N-ethoxycarbonyl-2-ethoxy-1,2-dihydroquinoline, or 1,1'-(carbonyldioxy)-dibenzotriazole.

Reactive functionally modified carboxy derivatives of the formula II can be manufactured in a manner known per se. For example, carboxylic acid halides, especially the carboxylic acid chloride, mixed anhydrides with a phosphoryl halide, especially the corresponding chlorine derivative, or mixed anhydrides with a carbonic acid semiester can be obtained by treating the carboxylic acid of the formula II, for example, with thionyl chloride or phosphorus pentachloride, with phosphorus oxychloride or with a chlorocarbonic acid lower alkyl ester, while for the manufacture of the carboxylic acid azide, the carboxylic acid of the formula II is reacted first with hydrazine and then with nitrous acid. The vinyl ester of the formula II can be obtained, for example, by transesterification of a corresponding lower alkyl ester, for example with vinyl acetate, a 1-lower alkoxy vinyl ester, especially 1-ethoxyvinyl ester, can be obtained by the ethoxyacetylene method, a 2-(N-lower alkylcarbamoyl)-1-hydroxysulphonylphenylvinyl ester can be obtained analogously to the Woodward method with a corresponding 1,2-oxazolium reagent, a phenyl(thio)ester can be obtained by the carbodiimide method from the carboxylic acid and the phenol or thiophenol, a 1-lower alkyl-2-pyridinium ester, especially 1-methyl-2-pyridinium ester, can be obtained, for example, by reaction with 2-chloro-1-methylpyridinium iodide in the presence of an amine base, a 1,3-di-lower alkyl- or 1,3-dicycloalkyl-2-isourea ester can be obtained by reacting the carboxylic acid with a corresponding diimide according to the carbodiimide method and a 1-di(phenyl)-lower alkyl-2-isourea ester can be obtained by treating the carboxylic acid with a corresponding cyanamide (cyanamide method), while a silyl ester can be formed, for example, with a corresponding chlorosilane.

In addition, it is possible to use as starting materials those compounds of the formula II in which X₁ is carbamoyl and to react these with a compound of the formula X₆—(CH₂)₂—N(R₁)(R₂) (IIb), or with a salt thereof, in which X₆ represents reactive esterified hydroxy.

Reactive esterified hydroxy denotes especially hydroxy esterified by a strong inorganic acid or organic sulphonic acid, for example halogen, such as chlorine, bromine or iodine, sulphonyloxy, such as hydroxysulphonyloxy, halosulphonyloxy, for example fluorosulphonyloxy, lower alkanesulphonyloxy optionally substituted, for example, by halogen, for example methane- or trifluoromethane-sulphonyloxy, cycloalkanesulphonyloxy, for example cyclohexanesulphonyloxy, or benzenesulphonyloxy optionally substituted, for example, by lower alkyl or halogen, for example p-bromophenyl- or p-toluene-sulphonyloxy.

$X_1$ of the formula II may also represent N-(2-$X_6$-ethyl)-carbamoyl, aziridin-1-ylcarbonyl or 2-oxazolin-2-yl. Corresponding starting compounds can be reacted with an amine of the formula $HN(R_1)(R_2)$ (IIc) or with a salt thereof, preferably in excess, to form the compound of the formula I.

In addition, the treatment of starting materials of the formula II in which $X_1$ represents 2-(N-$X_7$-aminoethyl)-carbamoyl and $X_7$ represents hydrogen or $R_1$ or $R_2$ with a compound of the formula $X_6$-$R_2$ or $X_6$-$R_1$, respectively, can result in the compound of the formula I.

The reactions described above may optionally be carried out in the presence of one of the bases mentioned above, the reactions being carried out especially in a temperature range of approximately from 20° C. to the boiling temperature of the reaction medium.

The N-substitution of compounds of the formula II in which $X_1$ represents 2-(N-$X_7$-aminoethyl)-carbamoyl can also be effected by reaction with lower alkanals or lower alkanones corresponding to $R_1$ or $R_2$. There come into consideration as lower alkanals and lower alkanones that correspond to the radicals $R_1$ and $R_2$, for example, formaldehyde or acetaldehyde or acetone, also corresponding, optionally etherified or esterified hydroxy-lower alkanals or hydroxy-lower alkanones or optionally esterified carboxy-lower alkanals or carboxy-lower alkanones.

The reaction is customarily carried out under reducing conditions, for example with hydrogen in the presence of a hydrogenation catalyst or with other reducing agents, especially with formic acid. Hydrogenation catalysts are, for example, sub-group elements of the Periodic System or their derivatives, preferably those of the VIIIth sub-group, such as palladium or platinum, or palladium or platinum dioxide, it being possible for the catalysts to be supported on suitable carriers, such as activated carbon, aluminium oxide or silica.

Variant b

The etherification can be carried out, for example, with the aid of a corresponding alkylating agent. As such agents there come into consideration, for example, compounds of the formula $R'_3$—$X_6$, $R'_3$ representing a radical derived from $R_3$, such as lower alkyl, $C_3$-$C_5$-alkenyl, $C_3$-$C_7$-cycloalkyl or $C_3$-$C_7$-cycloalkyl-lower alkyl, and $X_6$ having the meanings given hereinbefore. There preferably come into consideration lower alkyl halides, $C_3$-$C_5$-alkenyl-, $C_3$-$C_7$-cycloalkyl- or $C_3$-$C_7$-cycloalkyl-lower alkyl halides, such as methyl iodide, also di-lower alkyl sulphates, such as dimethyl sulphate, diazo-lower alkanes, such as diazomethane, tri-lower alkyl-sulphonium, tri-lower alkylselenium, tri-lower alkyl-oxosulphonium or tri-lower alkylanilinium hydroxides, such as trimethylsulphonium, trimethylselenium, trimethyloxosulphonium or trimethylanilinium hydroxide, or an alcohol corresponding to $R_3$, such as methanol.

When using compounds of the formula $R'_3$—$X_6$ and a di-lower alkyl sulphate, the etherification is carried out especially in the presence of one of the bases mentioned hereinbefore, preferably potassium carbonate, while the reaction with a diazo-lower alkane is carried out, if necessary, in the presence of a Lewis acid. Lewis acids are, for example, halides of boron, aluminium, tin(II), antimony(III), arsenic(III), silver(I), zinc(II) and iron-(III).

The etherification of the compound of the formula III with the aid of an alcohol derived from $R_3$, such as methanol, is carried out, for example, in the presence of a strong acid or, under anhydrous conditions, of a dehydrating agent, especially one of the type mentioned hereinbefore.

As strong acids there may be mentioned, especially, strong protonic acids, for example mineral acids, such as hydrohalic acids, sulphuric acid or a phosphoric acid, strong carboxylic acids, such as a lower alkanecarboxylic acid or a benzoic acid, each of which may optionally be substituted by halogen, for example glacial acetic acid or trifluoroacetic acid, or sulphonic acids, such as lower alkanesulphonic acid optionally substituted, for example, by halogen, of benzenesulphonic acid optionally substituted, for example, by halogen or by lower alkyl, for example p-toluenesulphonic acid.

Variant c

Depending on the choice of the starting material of the formula IV, the substitution of the diazonium grouping —$N_2^\ominus A^\ominus$ can be effected by treatment with a cyanide, a chloride or methanol.

If $X_2$ of the formula IV represents the diazotising grouping —$N_2^\ominus A^\ominus$, $X_3$ represents $R_4$ and $X_4$ represents $R_3$, cyano can be introduced, for example, by reaction with cyanides, for example analogously to the Sandmeyer reaction using copper(I) cyanide or alkali metal tetracyano cuprate(I) or in accordance with the Gattermann reaction using alkali metal cyanides in the presence of metallic copper.

The substitution of the diazonium group $X_3$ in compounds of th.e formula IV ($X_2$ represents $R_5$ and $X_4$ represents $R_3$), can likewise be carried out, for example, according to the Sandmeyer reaction, using copper(I) chloride or using chlorides, such as alkali metal chlorides, in the presence of copper metal according to Gattermann.

If, for example, compounds of the formula IV in which $X_2$ represents $R_5$, $X_3$ represents $R_4$ and $X_4$ represents the grouping —$N_2^\ominus A^\ominus$ are treated with an alcohol corresponding to $R_3$, $X_4$ is replaced by $R_3$.

In an advantageous modification of this process variant, the compounds of the formula IV can be formed in situ and reacted further under the particular reaction conditions, without being isolated, to form the compound of the formula I. First of all, corresponding amines of the formula IV are used as starting materials (one of the radicals $X_2$, $X_3$ and $X_4$ is amino and the others, corresponding to the substitution pattern of the compound of the formula I, represent $R_3$, $R_4$ or $R_5$) these are diazotise with nitrites, such as alkali metal nitrites, or nitro-lower alkanes in the presence of protonic acids, for example those of the type mentioned in Variant (b), and the compounds of the formula IV formed in situ are reacted further without being isolated, in the manner described in each case above, to form the compound of the formula I.

Advantageously, a reaction temperature of from approximately −10° to approximately +40° C. is selected for these reactions.

Variant d

A compound of the formula V can be converted, for example, by dehydration into the compound of the formula I or a salt thereof. Accordingly, $X_5$ of the formula V represents, for example, hydroxyiminomethyl or O-substitututed hydroxyiminomethyl, carbamoyl, N-monosubstituted carbamoyl or a corresponding thiocarbamoyl. Substituted hydroxyiminomethyl or substituted carbamoyl is formed especially in situ, the particular substituents being derived predominantly from the particular dehydrating agents used. Such radicals $X_5$ are, for example, tri-halo-lower alkanoyliminomethyl, or carbamoyl that is substituted by halosulphonyl, lower alkanesulphonyl or by unsubstituted or, for example, halo- or lower alkyl-substituted benzenesulphonyl or aminosulphonyl.

The dehydration is effected, for example, with the aid of a dehydrating agent that is customary for the formation of nitriles, the process preferably being carried out in the presence of one of the bases mentioned hereinbefore. Such dehydrating agents are listed in Synthesis 905f. (1978) and 748f. (1983). There may be mentioned by way of example mixed and symmetrical acid anhydrides, which are formed, for example, from substituted or unsubstituted lower alkanecarboxylic acids, sulphonic acids and/or mineral acids. Such acid anhydrides are, for example, tri-halo-lower alkanecarboxylic acid anhydrides, sulphonyl halides, such as sulphuryl halides, or phosphorus halides, such as phosphorus(III) or phosphorus(V) or phosphorus oxyhalides.

From among the dehydrating agents mentioned in connection with Variant (a) there may be mentioned, for example, dicyclohexylcarbodiimide, cyanuric chloride and 1,1'-dicarbonyldiimidazole.

The intermediates of the formula V, especially those in which $X_5$ represents hydroxyiminomethyl, O-substituted hydroxyiminomethyl or N-mono-substituted carbamoyl, are formed by processes known per se, most of them being formed in situ and reacted further under the reaction conditions by isolation to form the compound of the formula I.

For example, in a preferred embodiment of the above process variant, for example a compound of the formula V in which $X_5$ represents formyl can be used as starting material and treated with a hydroxylamine, especially an acid addition salt thereof, and with a suitable dehydrating agent. In so doing, there is first of all formed as an intermediate a compound of the formula V in which $X_5$ represents hydroxyiminomethyl which does not need to be isolated and reacts further according to the process under the action of the dehydrating agent.

The dehydration can initially be carried out while cooling, if necessary to $-78°$ C. especially when preceded by the formation of the aldoxime ($X_5=-CH=N-OH-$) from the corresponding formyl compound ($X_5=-CHO$); the reaction temperature can then be increased to the boiling temperature of the reaction medium.

The formation of the compound of the formula I and a salt thereof can also be effected by directly introducing the cyano group into the compound of the formula V in which $X_5$ is hydrogen, by reaction with a cyanogen halide, for example cyanogen chloride or bromide, or with cyanogen. This reaction is carried out using one of the above-mentioned Lewis acids as catalyst.

The invention relates especially to the processes described in the Examples.

If the mentioned starting materials have basic centres, it is also possible, for example, for acid addition salts to be formed, while starting materials having acidic groups form, for example, salts with bases.

Depending on the choice of reaction conditions, the starting materials can be used in free form or in the form of their salts or the compounds according to the invention having salt-forming properties can the obtained in free form or in the form of their salts.

For example, resulting acid addition salts can be converted in a manner known per se, for example by treatment with a base, such as an alkali metal hydroxide, into the free compound or, for example by treatment with suitable acids or derivatives thereof, into different salts. The resulting free compound having salt-forming basic properties can be converted into its salts, for example by treatment with acids or corresponding anion exchangers.

Owing to the close relationship between the salt-forming compounds in free form and in the form of their salts, hereinbefore and hereinafter free compounds and their salts should be understood as being optionally also the corresponding salts and free compounds, respectively, where appropriate with regard to meaning and purpose. Also included are salts that are unsuitable for pharmaceutical use, as these can be used, for example, for isolating and purifying free compounds according to the invention and their pharmaceutically acceptable salts.

The compounds according to the invention, including their salts, can also be obtained in the form of their hydrates, or their crystals can occlude, for example, the solvent used for crystallisation.

The invention also relates to those embodiments of the process according to which a compound obtainable as intermediate at any stage of the process is used as starting material and the remaining steps are carried out or a starting material is used in the form of a derivative or salt and/or its racemates or antipodes or, especially, is formed under the reaction conditions.

In the process of the present invention there are preferably used those starting materials which result in the compounds described at the beginning as being especially valuable. The invention relates also to novel starting materials, which were developed especially for the manufacture of the compounds according to the invention, to their use, for example as intermediates, and, if desired, as active ingredients of medicaments, and to processes for their manufacture.

The dosage of the active ingredient, which is administered alone or together with customary carriers and adjuncts, depends upon the species to be treated, its age and individual condition, and upon the method of administration. The single dose, for example for a mammal weighing approximately 75 kg, depending on the type of disease, individual condition and age, is preferably approximately 100 mg, for example in the case of oral administration.

The invention also relates to pharmaceutical preparations and processes for the manufacture of pharmaceutical preparations which contain as active ingredients compounds of the formula (I) or pharmaceutically acceptable salts of such compounds having salt-forming properties.

The pharmaceutical preparations according to the invention are those intended for enteral, such as peroral or rectal, administration and parenteral administration to warm-blooded animals. Suitable dosage unit forms, especially for peroral administration, for example dragées, tablets or capsules, preferably contain from approximately 1 mg to approximately 100 mg, especially from approximately 1 mg to approximately 25 mg, of a compound of the formula (I) or of a pharmaceutically acceptable salt of a corresponding compound capable of salt formation, together with pharmaceutically acceptable carriers.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch wastes using, for example, corn, wheat, rice or potato starch, gelatine, tragacanth, methylcellulose and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores can be provided with suitable coatings that may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the production of coatings that are resistant to gastric juices, solutions of suitable cellulose preparations, such as acetylcellulose phthalate or hydroxy-propylmethylcellulose phthalate. Colourings or pigments can be added to the tablets or dragée coatings, for example for identification purposes or to indicate different doses of active ingredient.

Further orally administrable pharmaceutical preparations are dry-filled capsules consisting of galatine and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers. Preferred are, inter alia, capsules that can be easily bitten through or swallowed without being chewed.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain viscosity-increasing substances, for example sodium carboxymethylcellulose, sorbitol and/or dextran, and, optionally, also stabilisers.

The pharmaceutical preparations of the present invention can be manufactured in a manner known per se, for example by means of conventional mixing, granulating, confectioning, dissolving or lyophilising processes.

For example, pharmaceutical preparations for oral administration can be obtained by combining the active ingredient with solid carriers, optionally granulating a resulting mixture, and processing the mixture or granulate, if desired or necessary after the addition of suitable adjuncts, to form tablets or dragée cores.

The following Examples described hereinbefore, but do not limit its scope in any way. Temperatures are given in degrees Celcius.

EXAMPLE 1

While stirring under nitrogen, at minus 30°, a solution of 23 g (0.1 mol) of 4-chloro-5-cyano-2-methoxybenzoic acid chloride in 70 ml of methylene chloride is added dropwise to a solution of 11.6 g (0.1 mol) of 2-diethylaminoethylamine in 100 ml of methylene chloride. The resulting white suspension is then stirred at room temperature for 15 hours, 105 ml (0.105 mol) of 1M sodium hydroxide solution are then added dropwise thereto and the whole is stirred until 2 distinct layers have formed and then separated in a separating funnel, and the aqueous phase is again extracted by shaking with 50 ml of methylene chloride. The combined organic phases are dried over magnesium sulphate and filtered, 150 ml of cyclohexane are added and methylene chloride is distilled off until the distillation temperature is 70°. After cooling, the base that has crystallised out is filtered off with suction and then washed with cyclohexane. After drying, 4-chloro-5-cyano-N-(2-diethylaminoethyl)-2-methoxybenzamide having a melting point of 104°–105° is obtained.

EXAMPLE 2

30 g of 4-chloro-5-cyano-N-(2-diethylaminoethyl)-2-methoxybenzamide are dissolved in 100 ml of acetone and, while stirring and cooling with ice, the pH is adjusted to 5 with ethereal hydrochloric acid, the hydrochloride crystallising out. The crystals are filtered off with suction and washed twice with a small amount of acetone, the salt is dried under a high vacuum at 60° and 4-chloro-5-cyano-N-(2-diethylaminoethyl)-2-methoxybenzamide hydrochloride having a melting point of 189°–190° (decomposition) is obtained.

EXAMPLE 3

25.5 g (0.1 mol) of N-(2-aminoethyl)-4-chloro-5-cyano-2-methoxybenzamide, 39 g (0.25 mol) of ethyl iodide and 41.5 g of potassium carbonate are stirred in 300 ml of ethanol for 15 hours at 50°. The ethanol is then concentrated by evaporation in a water-jet vacuum and 300 ml of methylene chloride and 150 ml of water are added to the residue. The layers are separated and the organic phase is extracted twice more by shaking with 100 ml of water each time. The methylene chloride solution is then dried over magnesium sulphate and concentrated by evaporation. Crude 4-chloro-5-cyano-N-(2-diethylaminoethyl)-2-methoxybenzamide remains as residue and, for purification, is recrystallised once from methylene chloride/cyclohexane. Melting point 104°–105°.

The starting material can be manufactured in a manner analogous to that described in Example 1:

N-(2-aminoethyl)-4-chloro-5-cyano-2-methoxybenzamide in the form of a colourless oil; hydrochloride m.p. 227o with decomposition; from 120 g (2 mol) of ethylenediamine in 250 ml of methylene chloride and 23 g (0.1 mol) of 4-chloro-5-cyano-2-methoxybenzoic acid chloride.

EXAMPLE 4

While stirring at room temperature, 0.63 g (7.2 mmol) of N-ethylisopropylamine is added to a solution of 1.62 g (6.8 mmol) of 2-methoxy-4-chloro-5-cyanobenzoic acid aziridide in 20 ml of toluene. The whole is then heated to 100° C. and stirred for a further 10 hours at this temperature. This reaction mixture is then allowed to cool, is diluted with 100 ml of methylene chloride and washed twice with 40 ml of water. The combined organic phases are dried over magnesium sulphate, filtered and then concentrated to dryness under reduced pressure. The resulting crude material is recrystallised once from methylene chloride/ether. 4-chloro-5-cyano-N-(2-ethylisopropylaminoethyl)-2-methoxybenzamide having a melting point of 103°–105° C. is thus obtained.

The starting material can be manufactured as follows:

While stirring at −60° C. and with the exclusion of moisture, a solution of 19.7 g (86 mmol) of 2-methoxy-4-chloro-5-cyanobenzoic acid chloride in 200 ml of methylene chloride is added dropwise over a period of 15 minutes to a solution of 3.9 g (90 mmol) of ethyleneimine and 15.3 ml (90 mmol) of ethylisopropylamine in 200 ml of methylene chloride. The reaction mixture is then allowed to warm up to room temperature and is stirred for a further hour at this temperature.

The reaction mixture is then diluted with 300 ml of methylene chloride and washed twice with 100 ml of water each time, and the organic phase is dried with magnesium sulphate, filtered and concentrated by evaporation. The resulting 2-methoxy-4-chloro-5-cyanobenzoic acid aziridide is recrystallised from methylene chloride/ether. 4-chloro-5-cyano-2-methoxybenzoic acid aziridide having a melting point of 132°–134° C. results.

EXAMPLE 5

In a manner analogous to that described in Example 4, 4-chloro-5-cyano-N-(2-methylethylaminoethyl)-2-methoxybenzamide having a melting point of 100°–102° C. is obtained from 3.6 g (15 mmol) of 2-methoxy-4-chloro-5-cyanobenzoic acid aziridide and 1.4 ml (16 mmol) of N-ethylmethylamine in 20 ml of toluene.

EXAMPLE 6

While stirring at 0° C., 2.7 g (19 mmol) of α-chloroethylchloroformate (cf. J. Org. Chem. 49, 2081 (1984)) are added dropwise to a solution of 4.7 g (12.7 mmol) of 4-chloro-5-cyano-N-(2-benzylethylaminoethyl)-2-methoxybenzamide (cf. Example 2) and 90 mg (0.6 mmol) of potassium carbonate in 200 ml of dichloroethane. The whole is then heated under reflux for 3 hours. The reaction mixture is then concentrated to dryness in vacuo, 200 ml of methanol are added to the residue and the whole is heated for 2 hours under reflux. Concentration is repeated, and the residue is taken up in 200 ml of 2N sodium hydroxide solution and extracted three times with chloroform. The combined organic phases are dried over magnesium sulphate, filtered and concentrated by evaporation. The resulting crude material is purified by chromatography over 200 g of silca gel using methylene chloride/methanol/ammonia in a ratio of 100:10:1. The fractions containing the desired product are combined and concentrated by evaporation. The residue is taken up in 50 ml of methanol and, while cooling, the pH is adjusted to 3 using hydrochloric acid. Ether is then added, the hydrochloride crystallising out. 4-chloro-5-cyano-N-(2-ethylaminoethyl)-2-methoxybenzamide hydrochloride having a melting point of 190°–192° C. is obtained.

EXAMPLE 7

1.23 g (10 mmol) of isopropyl bromide are added to a suspension of 3.2 g (10 mmol) of 4-chloro-5-cyano-N-(2-ethylaminoethyl)-2-methoxybenzamide hydrochloride and 2.8 g (20 mmol) of potassium carbonate in 50 ml of ethanol. The reaction mixture is then heated under reflux for 12 hours while stirring. The mixture is allowed to cool and is then filtered and concentrated to dryness. The residue is taken up in methylene chloride and then washed twice with water, dried over magnesium sulphate and concentrated by evaporation. After recrystallisation from methylene chloride/ether, 4-chloro-5-cyano-N-(2-ethylisopropylaminoethyl)-2-methoxybenzamide having a melting point of 103°–105° C. is obtained.

EXAMPLE 8

In a manner analogous to that described in Example 4, 4-chloro-5-cyano-N-(2-methyl-tert.-butylaminoethyl)-2-methoxybenzamide having a melting point of 137°–138.5° C. is obtained from 3.6 g (15 mmol) of 2-methoxy-4-chloro-5-cyanobenzoic acid aziridide and 1.4 g (16 mmol) of N-tert.-butlmethylamine.

EXAMPLE 9

In a manner analogous to that described in Example 4, 4-chloro-5-cyano-N-(2-tert.-butylisopropylaminoethyl)-2-methoxybenzamide hydrochloride having a melting point of 178°–179° C. is obtained from 3.6 g (15 mmol) of 2-methoxy-4-chloro-5-cyanobenzoic acid aziridide and 2.6 ml (16 mmol) of N-tert.-butylisopropylamine in 100 ml of toluene.

EXAMPLE 10

2.96 g (0.01 mol) of 4-chloro-5-cyano-N-(2-diethylaminoethyl)-2-hydroxybenzamide are suspended together with 2.06 g (0.015 mol) of potassium carbonate in 100 ml of acetone and 1.92 g (0.0125 mol) of diethyl sulphate are added. The reaction mixture is then heated at boiling point for 5 hours and then cooled and the insoluble salts are filtered off with suction. The filtrate is concentrated by evaporation in a water-jet vacuum, the residue is taken up in ethyl acetate, washed twice with brine, dried over magnesium sulphate and concentrated by evaporation. 4-chloro-5-cyano-N-(2-diethylaminoethyl)-2-ethoxybenzamide having a melting point of 131.5°–133° remains as the residue.

For the purpose of conversion into the hydrochloric, acid the base is dissolved in acetone and rendered clearly Congo-acidic with an ethanolic hydrochloric acid solution, 4-chloro-5-cyano-N-(2-diethylaminoethyl)-2-ethoxybenzamide hydrochloride precipitating. Melting point 179°–181°.

The starting material can be manufactured as follows:

While stirring and cooling at 15°–20°, a solution of 37.5 g (0.15 mol) of boron tribromide in 100 ml of methylene chloride is added dropwise in the course of 30 minutes to a solution of 23.9 g (0.1 mol) of 4-chloro-5-cyano-2-methoxybenzoic acid ethyl ester in 2 liters of methylene chloride. The reaction mixture is then stirred for a further 15 hours and 200 ml of ice-water are added. The aqueous phase is then adjusted to pH 8 with saturated soda solution. The 4-chloro-5-cyanosalicylic acid ethyl ester that precipitates is filtered off with suction and recrystallised from ethanol.

22.5 g (0.01 mol) of 4-chloro-5-cyanosalicylic acid ethyl ester are left to stand at room temperature for 15 hours in 110 ml of 1N sodium hydroxide solution, 500 ml of ethanol and 500 ml of water. The ethanol is then distilled off in a rotary evaporator and 60 ml of 2N hydrochloric acid are added to the remainder of the solution, 4-chloro-5-cyanosalicylic acid precipitating. 19.75 g (0.1 mol) of 4-chloro-5-cyanosalicylic acid are heated to boiling point together with 200 ml of chloroform and 40 ml of thionyl chloride. when the evolution of gas has ceased, the reaction mixture is concentrated by evaporation in a rotary evaporator and 4-chloro-5-cyano-N-(2-diethylaminoethyl)-salicylamide is manufactured in a manner analogous to that described in Example 1.

EXAMPLE 11

In a manner analogous to that described in Example 10, 4-chloro-5-cyano-N-(2-diethylaminoethyl)-2-n-propoxybenzamide having a melting point of 88°–89° is obtained from 2.96 g (0.01 mol) of 4-chloro-5-cyano-N-(2-diethylaminoethyl)-2-hydroxybenzamide, 2.06 g (0.015 mol) of potassium carbonate and 1.79 g (0.0105 mol) of n-propyl iodide in 100 ml of acetone; it can be converted into the hydrochloride having a melting point of 164°–166° by reaction with ethanolic hydrochloric acid solution in acetone.

EXAMPLE 12

In a manner analogous to that described in Example 10, 4-chloro-5-cyano-N-(2-diethylaminoethyl)-2-isopropoxybenzamide having a melting point of 61°–62° is obtained from 2.96 g (0.01 mol) of 4-chloro-5-cyano-N-(2-diethylaminoethyl)-2-hydroxybenzamide, 2.06 g (0.015 mol) of potassium carbonate and 1.79 g (0.0105 mol) of isopropyl iodide in 100 ml of acetone; it can be converted into the hydrochloride having a melting point of 141°–142° by reaction with ethanolic hydrochloric acid solution in acetone.

EXAMPLE 13

While stirring at 0°–5°, a solution of 2.3 g (0.01 mol) of 5-chloro-4-cyano-2-methoxybenzoic acid chloride in 7 ml of methylene chloride is added dropwise to a solution of 1.16 g (0.01 mol) of 2-diethylaminoethylamine in 10 ml of methylene chloride, and the reaction mixture is stirred for 2 hours at room temperature. 10.5 ml of 1N sodium hydroxide solution are then added, the layers are separated in a separating funnel, the organic phase is washed twice with water, dried over magnesium sulphate and concentrated by evaporation in a water-jet vacuum, 5-chloro-4-cyano-N-(2-diethylaminoethyl)-2-methoxybenzamide having a melting point of 97°–99° being obtained.

For the purpose of conversion into the hydrochloride, 3 g of 5-chloro-4-cyano-N-(2-diethylaminoethyl)-2-methoxybenzamide are dissolved in 20 ml of acetone and the solution is rendered weakly Congoacidic with an ethanolic hydrochloric acid solution, 5-chloro-4-cyano-N-(2-diethylaminoethyl)-2-methoxybenzamide hydrochloride precipitating. The latter is filtered with suction and then washed with a little acetone. Melting point 172°–174°.

The starting material can be manufactured as follows:

6.0 g (0.03 mol) of 4-chlorosalicylic acid ethyl ester are stirred at room temperature with 5 ml of sulphuryl chloride, sulphur dioxide and hydrogen chloride gases escaping. After 2 hours 2 ml of sulphuryl chloride and then, after 4½ hours, a further 2 ml of sulphuryl chloride are added and the whole is then stirred for 15 hours at room temperature. The excess sulphuryl chloride is then concentrated by evaporation in a water-jet vacuum, the crude 4,5-dichlorosalicylic acid ethyl ester, which is processed further directly, remaining.

7.05 g (0.03 mol) of 4,5-dichlorosalicylic acid ethyl ester are suspended together with 6.2 g (0.045 mol) of potassium carbonate in 75 ml of acetone and, while stirring, 4.56 g (0.036 mol) of dimethyl sulphate are added. The whole is then heated at boiling point for 5 hours. After cooling, the insoluble salts are filtered off with suction and the filtrate is concentrated by evaporation in a water-jet vacuum. The product is dissolved in chloroform, washed twice with water, dried over magnesium sulphate and concentrated by evaporation. As residue there remain 7.2 g of crude 4,5-dichloro-2-methoxybenzoic acid ethyl ester which, for the purpose of purification, is subjected to flash chromatography over 250 g of silica gel using petroleum ether/6% ethyl acetate (100 ml fractions). Fractions 12–17 elute pure 4,5-dichloro-2-methoxybenzoic acid ethyl ester having a melting point of 48°–50°.

2.49 g (0.01 mol) of 4,5-dichloro-2-methoxybenzoic acid ethyl ester and 1.0 g (0.11 mol) of copper(I) cyanide are heated at 220° for 7 hours while stirring in 8 ml of N-methyl-2-pyrrolidone. After cooling, the whole is poured onto ice-water and extracted with ethyl acetate, washed with water until neutral and dried over magnesium sulphate. After concentration of the ethyl acetate by evaporation, there remain 2.1 g of dark crude product which, for the purpose of purification, is subjected to flash chromatography over 150 g of silica gel with 8% ethyl acetate. 5-chloro-4-cyano-2-methoxybenzoic acid ethyl ester is eluted in fractions 30–39. Melting point 94°–96°.

2.4 g (0.01 mol) of 5-chloro-4-cyano-2-methoxybenzoic acid ethyl ester are left to stand for 15 hours at room temperature in 11 ml of 1N sodium hydroxide solution, 50 ml of ethanol and 50 ml of water. The ethanol is then distilled off in a rotary evaporator and 6 ml of 2N hydrochloric acid are added to the remaining solution, 5-chloro-4-cyano-2-methoxybenzoic acid precipitating. The latter is filtered off with suction, washed with water and dried in a dessicator over phosphorus pentoxide. Melting point 220°–222°.

2.1 g (0.01 mol) of 5-chloro-4-cyano-2-methoxybenzoic acid are heated at boiling point together together with 20 ml of chloroform and 4 ml of thionyl chloride. When no further evolution of gas can be detected, the whole is concentrated by evaporation in a rotary evaporator. The resulting crude 5-chloro-4-cyano-2-methoxybenzoic acid chloride is then processed further directly.

EXAMPLE 14

In a manner analogous to that described in Example 10, it is possible to manufacture:

4-chloro-5-cyano-2-cyclopentyloxy-N-(2-diethylaminoethyl)-benzamide, m.p. 161°–163°, from 2.96 g (0.01 mol) of 4-chloro-5-cyano-N-(2-diethylaminoethyl), salicylic acid amide, 1.66 g (0.012 mol) of potassium carbonate and 1.57 g (0.0105 mol) of bromocyclopentane in 50 ml of acetone;

4-chloro-5-cyano-2-cyclopropylmethoxy-N-(2-diethylaminoethyl)-benzamide, m.p. 152°–153°, from 2.96 g (0.01 mol) of 4-chloro-5-cyano-N-(2-diethylaminoethyl)salicylic acid amide, 1.66 g (0.012 mol) of potassium carbonate and 1.42 g (0.0105 mol) of cyclopropylmethyl bromide in 50 ml of acetone;

2-allyloxy-4-chloro-5-cyano-N-(2-diethylaminoethyl)benzamide, m.p. 145,5-147,5°, from 2.96 g (0.01 mol) of 4-chloro-5-cyano-N-(2-diethylaminoethyl)-salicylic acid amide, 1.66 g (0.0122 mol) of potassium carbonate and 6.09 g (0.0105 mol) of allyl bromide in 50 ml of acetone;

4-chloro-5-cyano-N-(2-diisopropylaminoethyl)-2-methoxy-benzamide, m.p. 176° (decomposition).

EXAMPLE 15

Tablets containing 25 mg of active ingredient, for example 4-chloro-5-cyano-N-(2-diethylaminoethyl)-2-methoxybenzamide, can be manufactured as follows:

| Constituents (for 1000 tablets) | |
|---|---|
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Manufacture

All the solid ingredients are first forced through a sieve having a mesh width of 0.6 mm. Then the active ingredient, the lactose, the talc, the magnesium stearate and half of the starch are mixed. The other half of the starch is suspended in 40 ml of water and this suspension is added to a boiling solution of the polyethylene glycol in 100 ml of water. The resulting starch paste is added to the main batch and the mixture, if necessary with the addition of water, is granulated. The granulate is dried overnight at 35°, forced through a sieve having a mesh width of 1.2 mm and pressed to form tablets having a diameter of approximately 6 mm that are concave on both sides.

EXAMPLE 16

Tablets containing 0.02 g of active ingredient, for example 4-chloro-5-cyano-N-(2-diethylaminoethyl)-2-methoxybenzamide, are manufactured as follows:

| Composition (for 10,000 tablets) | |
|---|---|
| active ingredient | 200.00 g |
| lactose | 290.80 g |
| potato starch | 274.70 g |
| stearic acid | 10.00 g |
| talc | 200.00 g |
| magnesium stearate | 2.50 g |
| colloidal silica | 32.00 g |
| ethanol | q.s. |

A mixture of the active ingredient, the lactose and 194.70 g of the potato starch is moistened with an ethanolic solution of the stearic acid and granulated through a sieve. After drying, the remainder of the potato starch, the talc, the magnesium stearate and the coilloidal silica are admixed and the mixture is pressed to form tablets each weighing 0.1 g which, if desired, can be provided with breaking grooves for finer adjustment of the dosage.

EXAMPLE 17

Capsules containing 0.025 g of the active ingredient, for example 4-chloro-5-cyano-N-(2-diethylaminoethyl)-2-methoxybenzamide, can be manufactured as follows:

| Composition (for 1000 capsules) | |
|---|---|
| active ingredient | 25.00 g |
| lactose | 249.00 g |
| gelatine | 2.00 g |
| corn starch | 10.00 g |
| talc | 15.00 g |
| water | q.s. |

The active ingredient is mixed with the lactose and the mixture is moistened uniformly with an aqueous solution of the gelatine and granulated through a sieve having a mesh width of 1.2–1.5 mm. The granulate is mixed with the dried corn starch and the talc and introduced in portions of 300 mg into hard gelatine capsules (size 1).

In a manner analogous to that described in the formulation Examples 15 to 17, it is possible to manufacture corresponding pharmaceutical preparations containing a compound of the formula I or a pharmaceutically acceptable salt thereof, especially a compound according to the invention according to any one of Examples 1 to 14.

We claim:

1. Benzamides of the formula

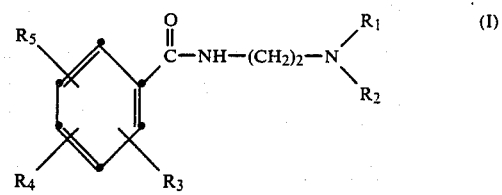

in which $R_1$ and $R_2$, independently of one another, each represents lower alkyl, $R_3$ represents lower alkoxy, $C_3$–$C_5$-alkenyloxy, $C_3$–$C_7$-cycloalkoxy of $C_3$–$C_7$-cycloalkyl-lower alkoxy, $R_4$ represents halogen and $R_5$ represents cyano and their salts.

2. Compounds according to claim 1 of the formula I in which $R_1$ and $R_2$, independently of one another, each represents lower alkyl having up to and including 4 carbon atoms, $R_3$ represents lower alkoxy having up to and including 4 carbon atoms, $C_3$–$C_5$-alkenyloxy, $C_3$–$C_7$- cycloalkoxy or $C_3$–$C_7$-cycloalkyl-lower alkoxy having up to and including 4 carbon atoms in the lower alkoxy moiety, $R_4$ represents halogen having an atomic number of up to and including 35 and $R_5$ represents cyano, and their salts.

3. Compounds according to claim 1 of the formula I in which $R_1$ and $R_2$, independently of one another, each represents lower alkyl having up to and including 4 carbon atoms, $R_3$ represents lower alkoxy having up to and including 4 carbon atoms, $R_4$ represents halogen having an atomic number of up to and including 35 and $R_5$ represents cyano, and their salts.

4. Compounds according to claim 1 of the formula

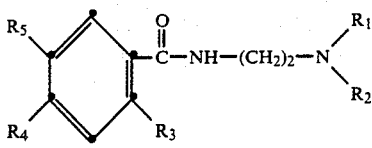

in which $R_1$, $R_2$, $R_3$, $R_4$ and $R_5$ have the meanings given in any one of claims 1 to 3, and their salts.

5. Compounds according to claim 1 of the formula Ia in which $R_1$ and $R_2$, independently of one another, each represents lower alkyl having up to and including 4 carbon atoms, $R_3$ represents methoxy or ethoxy, $R_4$ represents chlorine and $R_5$ represents cyano, and their salts.

6. Compounds according to claim 1 of the formula Ia in which $R_1$ and $R_2$ represent lower alkyl, especially lower alkyl having up to and including 4 carbon atoms, $R_3$ represents methoxy, $R_4$ represents chlorine, and $R_5$ represents cyano, their salts.

7. Compounds according to claim 1 of the formula I or Ia in which $R_1$ and $R_2$, independently of one another, each represents lower alkyl, the sum of the number of carbon atoms in the lower alkyl radicals being from 4 up to and including 6, and their salts.

8. Compounds according to claim 1 of the formula I or Ia in which $R_1$ and $R_2$, independertly of one another, each represents ethyl or isopropyl, and their salts.

9. A compound as claimed in claim 1 being 4-chloro-5-cyano-N-(2-diethylaminoethyl)-2-methoxy-benzamide or a salt thereof.

10. A compound as claimed in claim 1 being 4-chloro-5-cyano-N-(2-ethylisopropylaminoethyl)-2-methoxybenzamide or a salt thereof.

11. A compound as claimed in claim 1 being 4-chloro-5-cyano-N-(2-diethylaminoethyl)-2-isopropoxybenzamide or a salt thereof.

12. A compound as claimed in claim 1 being 4-chloro-5-cyano-2-cyclopentyloxy-N-(2-dietyylaminoethyl)-benzamide or a salt thereof.

13. A compound as claimed in claim 1 being 4-chloro-5-cyano-2-cyclopropylmethoxy-N-(2-diethylaminoethyl)-benzamide or a salt thereof.

14. A compound as claimed in claim 1 being 2-allyloxy-4-chloro-5-cyano-N-(2-diethylaminoethyl)-benzamide or a salt thereof.

15. A compound as claimed in claim 1 being 4-chloro-5-cyano-N-(2-diisopropylaminoethyl)-2-methoxy-benzamide or a salt thereof.

16. A compound as claimed in claim 1 being 4-chloro-5-cyano-N-(2-methyl-tert.-butylaminoethyl)-2-methoxybenzamide or a salt thereof.

17. A compound as claimed in claim 1 being 4-chloro-5-cyano-N-(2-diethylaminoethyl)-2-ethoxybenzamide or a salt thereof.

18. An anti-depressive and anti-schizophrenic pharmaceutical composition comprising an effective amount of a compound according to claim 1 or a pharmaceutically acceptable salt thereof in addition to a pharmaceutically acceptable carrier.

19. A method for treating of depressive states and schizophrenia in warm-blooded animals comprising treating warm-blooded animals in need of such treatment with an effective amount of a compound according to claim 1 or a pharmaceutically acceptable salt thereof.

* * * * *